(12) United States Patent
Frikart et al.

(10) Patent No.: US 8,971,958 B2
(45) Date of Patent: Mar. 3, 2015

(54) WEB-ENABLED PORTABLE MEDICAL DEVICE

(75) Inventors: Marcel Frikart, Bern (CH); Markus Jungen, Bolligen (CH)

(73) Assignee: Roche Diagnostics International AG, Rotkreuz (CH)

( * ) Notice: Subject to any disclaimer, the term of this patent is extended or adjusted under 35 U.S.C. 154(b) by 1987 days.

(21) Appl. No.: 11/870,216

(22) Filed: Oct. 10, 2007

(65) Prior Publication Data

US 2008/0091175 A1     Apr. 17, 2008

Related U.S. Application Data

(63) Continuation of application No. PCT/CH2005/000204, filed on Apr. 11, 2005.

(51) Int. Cl.
| | | |
|---|---|---|
| *H04M 1/00* | (2006.01) | |
| *H04L 29/06* | (2006.01) | |
| *G06F 19/00* | (2011.01) | |
| *A61M 5/142* | (2006.01) | |
| *A61M 5/178* | (2006.01) | |

(52) U.S. Cl.
CPC .......... *H04L 63/061* (2013.01); *G06F 19/3418* (2013.01); *A61M 5/14244* (2013.01); *A61M 5/14276* (2013.01); *A61M 5/178* (2013.01); *A61M 2205/3569* (2013.01); *A61M 2205/3584* (2013.01)
USPC .............. 455/556.1; 370/259; 604/890.1; 604/891.1; 604/892.1; 600/300; 600/301

(58) Field of Classification Search
USPC ........ 455/556.1; 600/300, 121, 131; 705/2, 3, 705/75; 709/203, 218
See application file for complete search history.

(56) References Cited

U.S. PATENT DOCUMENTS

| | | | | |
|---|---|---|---|---|
| 6,519,241 | B1 * | 2/2003 | Theimer ...................... | 370/338 |
| 6,558,321 | B1 * | 5/2003 | Burd et al. ................... | 600/300 |
| 7,040,318 | B2 * | 5/2006 | Dascher et al. ........... | 128/204.21 |
| 2004/0054263 | A1 * | 3/2004 | Moerman et al. ............. | 600/300 |

FOREIGN PATENT DOCUMENTS

| | | |
|---|---|---|
| WO | 02068015 | 9/2002 |
| WO | 03013635 | 2/2003 |
| WO | 2005009514 | 2/2005 |

OTHER PUBLICATIONS

Ordonez A. et al., "Use of a Telemedicin Device for the Care of Diabetic Patients", Program and Abstracts of the Annual Meeting of the European Association for the Study of Diabetes, Oct. 2, 1999, pp. 228.

* cited by examiner

*Primary Examiner* — Golam Sorowar
(74) *Attorney, Agent, or Firm* — Dinsmore & Shohl LLP

(57) ABSTRACT

A portable personal medical device, e.g., a wearable insulin pump, is provided with a web server and is controllable over a network by a browser equipped client, thereby enabling comprehensive and comfortable control, operation and/or configuration of the device.

45 Claims, 5 Drawing Sheets

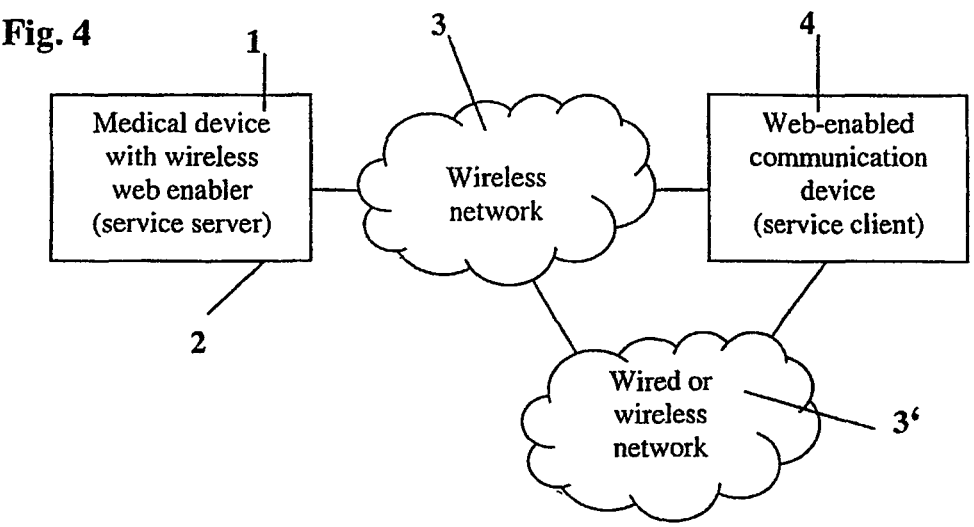
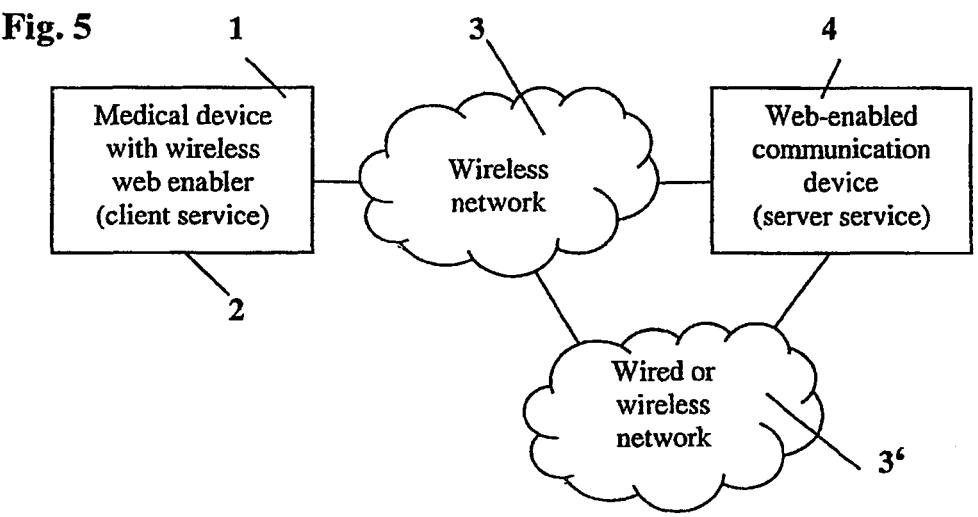

WEB-ENABLED PORTABLE MEDICAL DEVICE

CROSS REFERENCE TO RELATED APPLICATION(S)

This application is a continuation application of International Application No. PCT/CH2005/000204, filed Apr. 11, 2005 and published as WO 2006/108304 A1 on Oct. 19, 2006, and claims the priority thereof, the subject matter of which is hereby incorporated by reference in its entirety.

BACKGROUND

The present invention relates to devices for injecting, delivering, dispensing, infusing or administering a substance, and to methods of making and using such devices. More particularly, the present invention relates to a portable or wearable or implantable or semi-implantable medical device, in some embodiments, a pocket-size or less than pocket-size medical device, such as, for example, a wearable, pocket-size insulin infusion pump. The invention further relates to methods for operating and/or controlling such a medical device.

Portable medical devices, for example pocket-size devices that can be carried on the body of a person, are known. One example is insulin pumps for the external infusion pump therapy for people with diabetes. Other such portable, pocket-size devices are blood glucose measurement devices or diabetes management devices (DM) also used in diabetes treatment. It is already known to provide a remote controller for insulin pumps, so that certain functions can be operated by remote control, helping the user to control a pump that is concealed under his clothing (WO 2000/018977). However, such a remote control is a dedicated additional part or device that has to be carried by the user of the pump and the functionality of such a dedicated remote control is limited.

In hospital environments with wired networks or wireless local area networks (WLAN) it has been proposed recently to provide a separate web server box to link a stationary hospital infusion pump and an oxymeter to the network, so that a remote personal computer could monitor a patient's status.

SUMMARY

It is an object of the present invention to provide a personal portable or wearable or implantable or semi-implantable medical device that provides a comfortable and comprehensive way for a user or care-giver to operate and/or control the device. It is a further object of the present invention to provide methods for setting, controlling and monitoring personal medical devices, including small personal medical devices.

In one embodiment, the present invention comprises a portable or wearable or implantable or semi-implantable medical device, e.g., a pocket-size or less than pocket-size medical device, comprising a housing and a control unit within the housing adapted to control the medical device, e.g., its functional units or components, and within the housing, a wireless web enabler unit including a wireless interface control unit including a receiver and a transmitter for wirelessly receiving and transmitting information, e.g., data/messages/web-content, and a web enabler unit coupled to the wireless interface control unit and coupled to the control unit, wherein the wireless interface control unit and web enabler unit are configured to connect the control unit to a web based wireless network so that the medical device is wireless web-enabled.

In one embodiment, the present invention comprises a pocket-size or less than pocket-size medical device incorporating wireless web enablement directly within its housing.

By such a personal pocket-size medical device (for example, 7×5×2 cm, typical mobile phone size, or similar size) with its own embedded web server within the housing of the device which will connect to the network wirelessly, the device can be interrogated and/or controlled by any device which can connect to the network and is able to display or otherwise handle the web pages of the personal medical device. In a preferred embodiment, the device is a personal portable insulin pump and, in another preferred embodiment, the device is a blood glucose measurement device or diabetes management device.

In another embodiment the medical device is adapted for delivering a liquid on a one dose or per dose basis, e.g., an insulin or injection pen.

In a preferred embodiment, the wireless web enabler unit is adapted to work with an application layer protocol over TCP and/or UDP over IP (TCP/IP stack). The device can be configured to communicate using a network protocol such as HTTP, HTTPS, FTP, NTP, SMTP, POP3, Telnet, DNS, SNMP, RIP, IPFIX or another internet application layer protocol for applications based on client or server services using the mentioned protocols. In some preferred embodiments, the browser-equipped client that allows the wearer of the medical device to configure and/or control and/or interrogate the device is selected from the group consisting of a cell phone, a smart phone, a personal digital assistant (PDA), a laptop computer, a tablet computer (tablet PC), a desktop computer or another web browser equipped device and browser-less devices, with e.g. java-based microbrowser technology, in this way giving the wearer a comfortable management of the medical device by any browser equipped device that he or she has access to and without needing a dedicated control device that serves only as remote control for the medical device.

It is further possible that the wireless web enabler unit of a medical device in accordance with the present invention is configured as web client to use an internet service from a server via the wireless network, for example the wireless web enabler unit is configured as NTP client to query a time server. In a preferred embodiment, the wireless interface control unit is configured to communicate using RF technology and may be configured to communicate using Bluetooth® technology. The medical device may, in this case, be adapted so that the wireless interface control unit is configured to communicate using "Bluetooth PAN" profile (TCP/IP over Bluetooth with BNEP=Bluetooth Network Encapsulation Protocol).

In another embodiment of a medical device in accordance with the present invention, the wireless interface control unit is configured to communicate using ZigBee, RFID, HomeRF, WLAN, UWB, NFC or other non-Bluetooth RF technology or is configured to communicate using wireless non RF technology, e.g., infrared beams.

The wireless web enabler unit of the medical device may be based on a single-processor or may be set up on two or more different processors. The wireless web enabler unit can be configured as a gateway computer consisting of a web server with CGI functionality wherein the communication with the medical device processor is done by using a proprietary protocol over a serial interface. Alternatively, the wireless web enabler unit can be built in the medical device processor unit to provide direct network connectivity without the need of a serial interface connection between the medical device processor unit and the web enabler unit as modem using a network dial-up architecture to connect the medical device processor unit over the modem to the network. The wireless web enabler unit of the device may further comprise the interface between the web enabler unit and the medical device control unit (CGI=common/uncommon gateway interface).

In a preferred embodiment, the interface generates commands for the medical device control unit according to data and/or information and/or web content received from the web enabler unit (command generation by web enabler). In a further embodiment, the interface generates data and/or information and/or web content for the web enabler unit according to commands received from the medical device control unit (dynamic web page content generation by the web enabler).

In some preferred embodiments, the wireless web enabler unit is configured to prevent data interchange with an unauthorized device and/or user using the wireless network in order to provide standards-based internet security in combination with the security provided by the wireless network itself. In another embodiment, the wireless web enabler unit is configured to use secure communications (encryption, etc.), such as VPN, IPSec, SSH (Secure Shell), SSL (Secure Sockets Layer), etc., thus adding enhanced standard internet security.

In some embodiments, the present invention comprises methods allowing full control of a wearable personal pocket-size medical device. To this end, in a first method for controlling a portable or wearable or implantable or semi-implantable medical device, e.g., a pocket-size or less than pocket-size medical device, the method comprises serving at least one web page using the at least one embedded web server contained within the medical device configured to enable a browser-equipped client to configure the medical device control unit via a network (health care provider (HCP) configuration & patient configuration tool), and changing the configuration/settings/parameters of the medical device control unit in response to a client interaction with the at least one web page.

In another embodiment according to the present invention, the method for controlling a portable or wearable or implantable or semi-implantable medical device, e.g., a pocket-size or less than pocket-size medical device comprises the steps of serving at least one web page using an embedded web server configured to enable a browser-equipped client to operate/control the medical device control unit via a network and changing the behavior/operation/status of the medical device control unit in response to a client interaction with the at least one web page.

In another embodiment according to the present invention, the method for uploading data of a portable or wearable or implantable or semi-implantable medical device comprises the steps of initiating a connection from a local service client to a remote service server over the wireless network in order to send one or more data packets from the medical device to the remote server.

Another embodiment for controlling a portable or wearable or implantable or semi-implantable medical device, e.g., a pocket-size or less than pocket-size medical device, may comprise the steps serving at least one web page using an embedded web server configured to enable a browser-less client to operate/control the medical device control unit via a network and changing the behavior/operation/status of a medical device control unit in response to a client interaction with the at least one web page. In this embodiment of the method, the browser-less client may be selected from the group consisting of a KeyFob, a watch, a BeltFob, a blood glucose meter (BGM), a continuous measurement device CM, a diabetes management device DM, a communication adapter, a connectivity add-on, a cell phone, a smart phone, a personal digital assistant (PDA), a laptop computer, a tablet computer (tablet PC), a desktop computer or any other web browser-less device. For other methods, the browser-equipped client may be selected from the group consisting of a cell phone, a smart phone, a personal digital assistant (PDA), a laptop computer, a tablet computer (tablet PC), a desktop computer or any other web browser equipped device which may be a BGM, a CM or a DM as well.

In some preferred embodiments of the present invention, the medical device is an insulin pump and the configuration change via the network is enabled for parameter settings of the insulin pump and/or basalrate change of the insulin pump and/or time and date settings of the insulin pump. In another preferred method, the medical device is a blood glucose measurement device.

In some preferred embodiment, the method comprises transferring data stored in the medical device control unit to the browser-equipped client in response to a client interaction with the at least one web page, and the medical device is an insulin pump and the data includes pump-history read-out and/or firmware version and/or status information. The medical device may be a blood glucose measurement device and the data includes history read-out and/or firmware version and/or status information.

A preferred method includes that the network is a wireless personal, local or wide area or a combination of two or more such networks or a combination of such a network with one or more wired networks. In some preferred embodiments, the network is a Bluetooth® personal area network (PAN) and the medical device represents a group network (GN) and the browser-equipped client represents a personal area network user (PANU) and/or the medical device represents a PANU and the browser-equipped device represents a GN and/or a NAP (network access point).

In embodiments wherein the medical device is an insulin pump, the controllable functions may include bolus delivery/read-out, basal profile change/read-out, pump mode change/read-out, and/or status output. If the medical device is a blood glucose meter, the controllable functions include blood glucose measurement value output and/or blood glucose measurement value readout.

In a preferred embodiment of the method, it comprises sending operation information from a medical device control unit to a browser-equipped client without a client interaction with the at least one web page. When the medical device is a insulin pump, the operation information may include alarm output and/or basal-rate-change output.

A method in accordance with the present invention may further comprise the steps of uploading a blood glucose value web-based from a blood glucose measurement device to an insulin pump. Further data of a blood glucose meter and/or an insulin pump may be web-based stored and/or retrieved centrally in a central storage media. Still further, the medical device can be a web client and may provide itself with time and/or date by interrogating a time server using a proprietary or standards based protocol such as NTP, SNTP, DTP or the like.

BRIEF DESCRIPTION OF THE DRAWINGS

FIG. 4 shows a medical device web service usage by a web-enabled communication device;

FIG. 5 shows a communication device web service usage by a web-enabled medical device;

DETAILED DESCRIPTION

In the context of the present invention, the term medical device comprises any device used in the practice of medicine, including, but not limited to, generally small, portable devices, e.g., insulin pumps or other personal medication pumps. Such insulin and other personal medication pumps are known in the state of the art and will not be described in their mechanical and electrical construction in detail unless necessary for the present invention. Another example of a small portable device related to the present invention are blood sugar meters (BGM), which are hand-held devices that test blood glucose levels, usually by placing a drop of blood (obtained by pricking a finger) on a small strip that is inserted in the meter. The meter calculates and displays the blood sugar level. Other examples of medical devices with which the present invention may be concerned are continuous monitoring (CM) devices for continuously monitoring blood glucose levels, insulin pens for injecting doses of insulin, and data or diabetes manager (DM) tools or devices. As appropriate, any of the aforementioned exemplary devices, and/or their functions, may be combined in one device.

Figure 1:
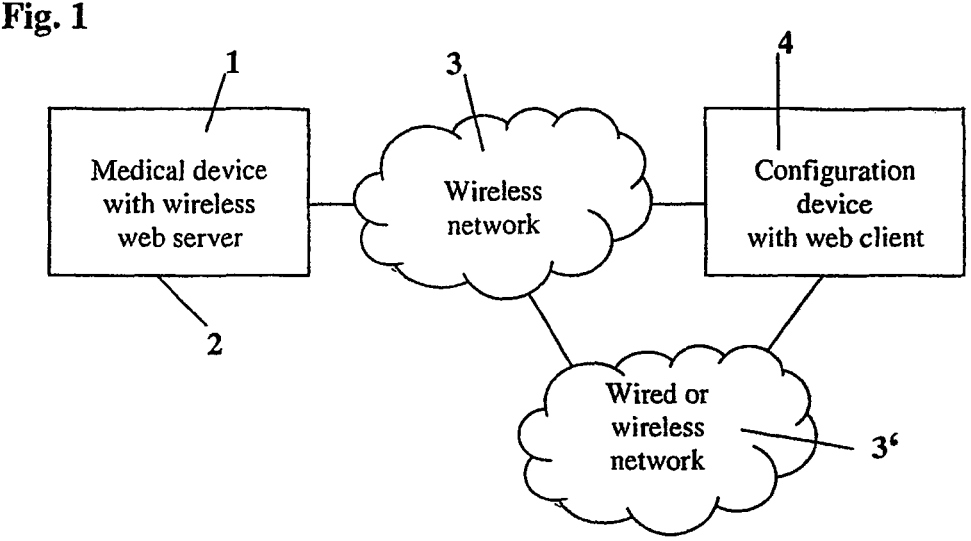
FIG. 1 shows a general representation of a medical device which can be configured over a network.

FIG. 1 shows, in representational form, a personal portable and wearable or implantable or semi-implantable medical device 1 with a housing 2. Generally, the device is a pocket size or less than pocket size medical device; however, the devices, components, methods and principles of the present invention may be incorporated with or useful for larger devices as well. A preferred a pocket size or less than pocket size medical device is an infusion device, e.g., an insulin pump. Another preferred device is a blood glucose meter.

According to the present invention, the device 1 is web-enabled so that a device 4 which is able to access the network 3 with a browser or even without a browser can exchange data over the network with medical device 1. Device 4 can, for example, be a cellular phone, a personal computer a personal digital assistant (PDA) or another browser equipped client. The network 3 may be a personal area network (PAN) in the form of a wireless PAN and, in some preferred embodiments, in the form of a Bluetooth® PAN. The network may further be a wireless local area network (WLAN) or may be a non-local network like a metropolitan area network, a wide area network, a global area network or a virtual private network. The device 4 may access the network 3 via another network 3'.

In a preferred method to control a medical device 1 by a browser equipped client 4 over network 3, the medical device is configurable by device 4 so that this device is, in this embodiment, a configuration device that allows configuration of the medical device over the web-pages provided by the embedded web-server of the medical device. In one preferred embodiment of the method, the medical device is configured by providing at least one configuration web-page by the embedded web-server of the medical device which configuration page allows the user of the configuration device, for example, to click on setting suggested by the web-page or to enter settings on the web-page so that configuration data is provided to the embedded web-server of the medical device. Such configuration can be divided into different groups that may be accessible only to medical personal or may be accessible to the patient in a more limited way than for the medical personal. Entering the configuration settings on the web-page will then change the configuration of the medical device control unit which actually controls the device in response to the client interaction by device 4 with the at least one web page. In this way all configurationable parameters of the medical device can be set or changed. In case of an insulin pump as medical device, such a configuration change may, for example, include the basal rate change or time/date settings.

Figure 9:
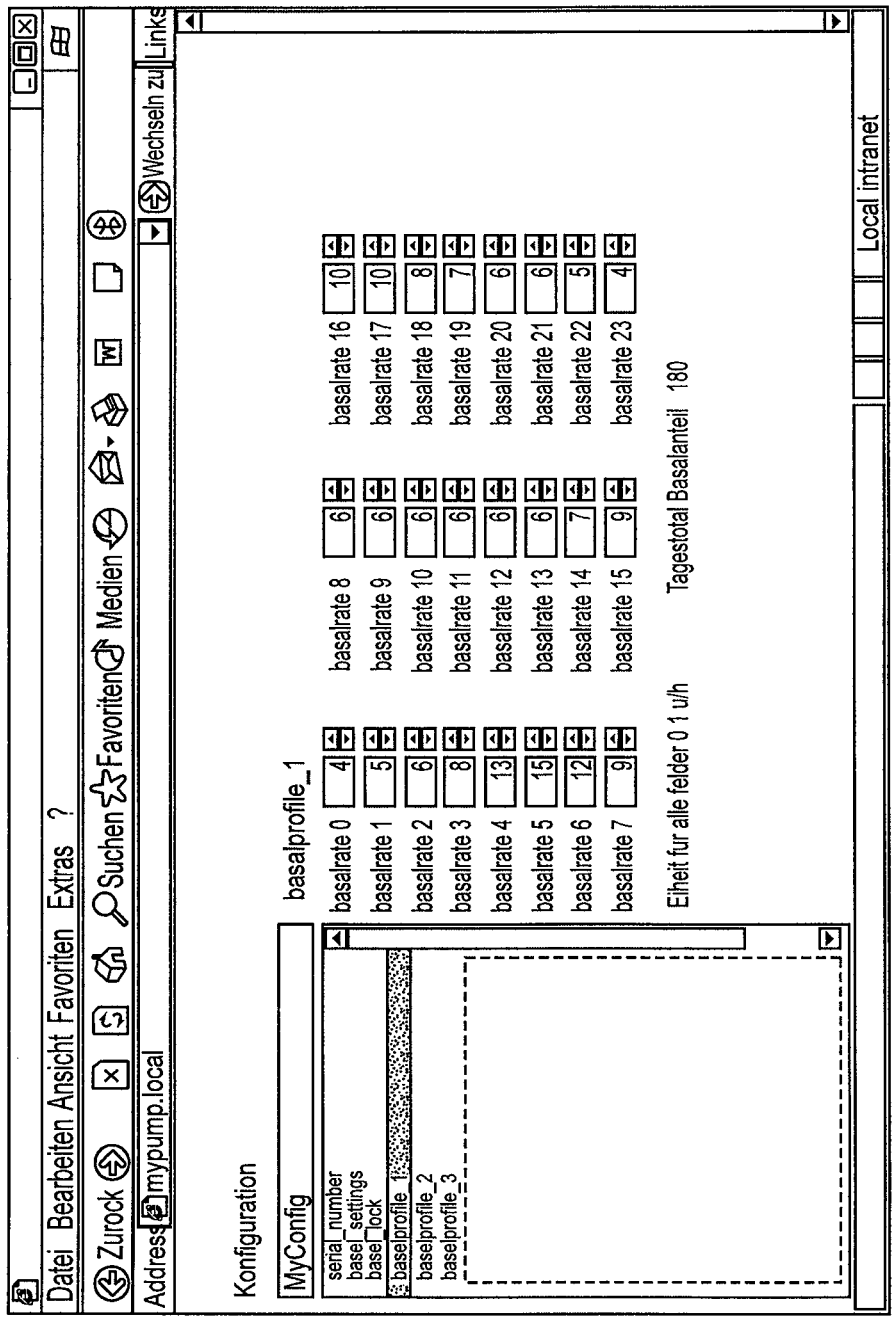
FIG. 9 shows an example of a pump configuration web page.

FIG. 9 shows an example of an configuration page provided by the medical device (insulin pump) and accessible by the configuration device. A number of configurable pump configurations are shown that are well known to one skilled in the art. As known from web pages, the functions of the medical device, e.g., insulin pump, to be configured can be selected on the page and can be modified, for example by the up and down buttons for the respective fields shown. When the page has been modified accordingly the pump will take over the configuration settings from its web server. It is of course further possible to transfer data stored in the medical device control unit by the embedded web-server to the client 4 by interaction with at least one web-page provided to this end. Such data may include pump history readout, firmware version readout or status information.

Figure 2:
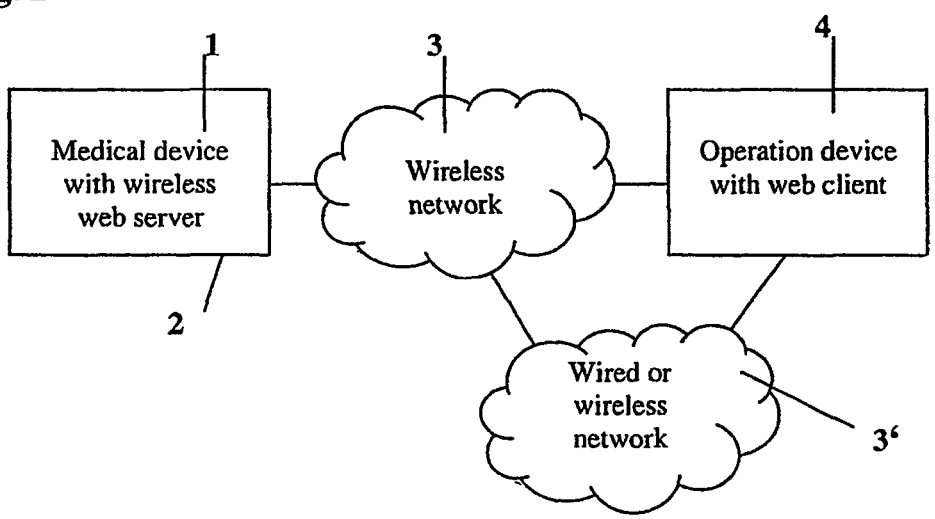
FIG. 2 shows a similar representation for the operation and control of a medical device.

FIG. 2 shows another embodiment of a method of controlling a medical device 1 with an embedded web-server included in the housing 2, wherein the medical device is not configured but operated and controlled by the same or another device 4 which case is used as operation device for the medical device 1. In this case, the embedded web-server provides at least one page that allows to readout or to change operational data of the medical device so that the medical device can actually be controlled in its operation. In this case, the medical device control unit will change its operation (functions) in response to a client interaction with the corresponding web-page provided by the embedded web-server of medical device 1. In case of an insulin pump, such functions can, for example, be pump rc bolus and bolus delivering settings which can be controlled by the browser equipped client 4 so that the pump will operate at the selected or entered bolus value. Of course, in this operation mode it will be possible to also get status read out function on the web-page and to effect status output towards the client 4 by selecting the corresponding field on the web-page. In case of a blood glucose meter, for example, a value readout can be selected by browsing with the client on the corresponding web-page of the embedded web-server of the BGM.

In another embodiment of the present invention, the operation device 4 is a browser-less client which is, for example, a KeyFob, a watch, a BeltFob, a blood glucose meter, a diabetes manager DM or a CM. In this case, the network may be any wireless network, e.g. a wide area network, for example a Bluetooth® PAN network.

Figure 3:
FIG. 3 shows a similar representation of configuration and/or operation/control of a medical device.

FIG. 3 shows an embodiment according to the present invention wherein the portable medical device 1 is used by another medical device 4. FIG. 4 shows the medical device web service usage by a web-enabled communication device, and FIG. 5 shows the communication device web service usage by a web-enabled medical device.

Figure 8:
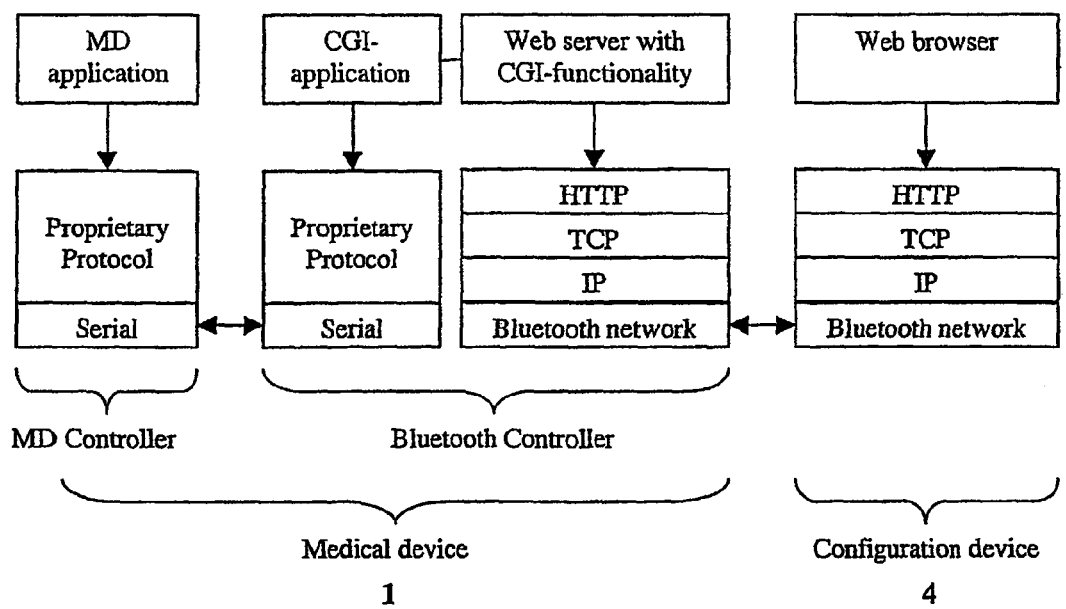
FIG. 8 shows an example of end-to-end communication of a configuration system with a build-in Bluetooth® controller with web server capability.

FIG. 8 shows another representation wherein the medical device (MD) is an infusion device (ID) and the client device 4 is a configuration device and wherein the wireless communication is provided by Bluetooth®. In this representation, the per se well known different protocol layers of the new web-enabled medical device 1 and of the client device 4 are shown with the application layer HTTP, the transport layer TCP/UDP, the internet layer IP and the network layer BNEP. Communication takes place over the Bluetooth® base band and Bluetooth® radio frequency and ports may be provided by the Bluetooth® module to the controller 5 of the medical device. In case of an infusion device such as an insulin pump, the infusion device controller actually controls the mechanical and electrical elements of the medical device that provide the necessary functionality. In one preferred embodiment of an infusion device, the MD controller controls the electric motor or motors that provide the actual pumping of the content of a infusion fluid contained within the infusion device.

Figure 6:
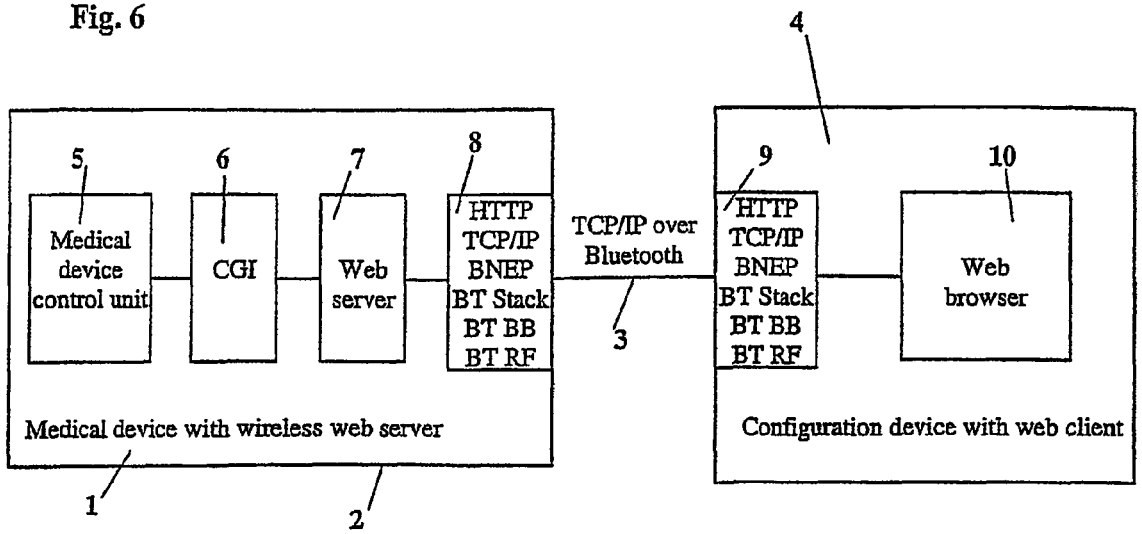
FIG. 6 shows a schematic representation of a configuration system for a medical device over a Bluetooth® network.

FIG. 6 shows a simplified block diagram of the elements of the medical device 1 with the housing 2 wherein these elements are provided together with other mechanical and electrical elements that are not shown. The infusion device controller controlling the other mechanical and electrical elements is depicted as box 5. This controller communicates over the server interface (CGI) 6 with the web-server 7. This web-server connects to the net 3 via the TCP/IP Bluetooth® module 8. On the side of the client device 4, which is labeled here as configuration device, but, of course, can as well be the operation device explained earlier, the connection to the net 3 is as well provided by a Bluetooth® TCP/IP module 9 which communicates with the web-browser application 10. All these elements are well known to those skilled in the art and it is therefore not necessary to elaborate more on their functionality and detailed construction.

Figure 7:
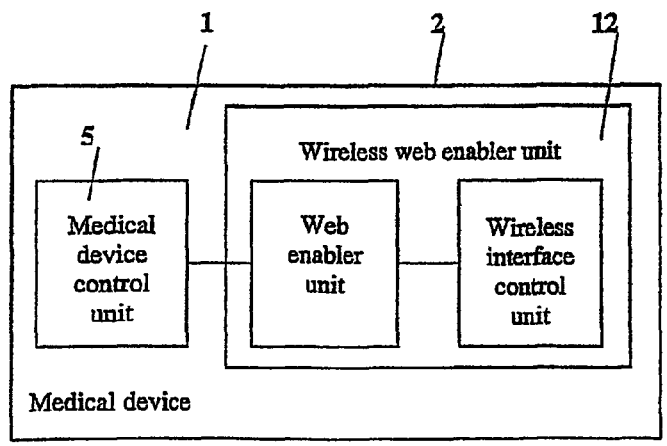
FIG. 7 shows a schematic view of a hardware solution.

FIG. 7 shows the medical device 1 and the wireless web-enabler unit as a block 12 within medical device 1, which block 12 is connected to the medical device control unit 5. The labeled blocks are well known to those skilled in the art and need no further elaboration on their construction and their function. The MD controller 5 connects to all or selected controllable electrical and mechanical elements of the medical device 1 which are included within and on housing 2 (not shown, but are well known to those skilled in the art of medical devices, including portable insulin pumps). A power supply of the portable personal device 1 is, of course, included, but is not shown.

Preferred embodiments of the present invention provide for a Bluetooth® web-based user interface in an insulin pump and for pump operation by off-the-shelf personal devices such as a PC, a PDA or a Smartphone. Further, a Bluetooth® web-based user interface in an insulin pump for the pump configuration is provided by off-the-shelf devices such as a PC, a PDA, a Smartphone. Further, a Bluetooth® web-based user interface in an insulin pump for its remote pump configuration by a PC over LAN, WAN, WWAN or Access Point is provided. Further, a Bluetooth® web-based pump operation by a KeyFob or a Bluetooth® web-based pump operation by DM (diabetes management) tools is provided. Further, a Bluetooth® web-based blood glucose (BG) value upload from a blood glucose meter (BGM) or from a continuous monitor device (CM) to the insulin pump is provided. Further, a Bluetooth® web-based centralized data storage (over an access point and by a LAN/WAN/WWAN on a server storing such data is provided.

In some preferred embodiments, the wireless web enabler unit is based on a single-processor, which may be a csr (Cambridge Silicon Radio Lt.) BlueCore BlueLab stand-alone VM application. The wireless interface control unit may be setup on two different processors and may be a csr (Cambridge Silicon Radio Lt.) BlueCore BCHS host SW solution. The wireless web enabler unit further comprises an interface between the web enabler unit and the medical device control unit which is a CGI=common gateway interface. The interface generates commands for the medical device control unit according to data and/or information and/or web content received from the web enabler unit. The interface may generate data and/or information and/or web content for the web enabler unit according to commands received from the medical device control unit so that there is dynamical web page content generation by the web enabler. Preferably, the network is a Bluetooth® personal area network (PAN) and the medical device represents a group network (GN) and the browser-equipped client represents a personal area network user (PANU).

The following terms used before or generally related to the field of web enablement are well known to the persons skilled in the art:
Personal Area Networks (PAN)
Wireless LAN (WLAN)
Virtual Private Network (VPN)
client-server-system: the client establishes a connection to the server. The client provides the user interface to the application. The server provides the functionality.
server-program: a program that implements a service.
internet-protocols:
application layer: HTTP, HTTPS, FTP, SMTP, POP3, TELNET, DNS, SNMP, RIP, IPFIX.
transport layer: TCP, UDP, SCTP.
network layer: IP (IPV4, IPV6)
application layer protocols
HTTP—Hypertext Transfer Protocol
FTP—File Transfer Protocol
SSH—Secure Shell
SMTP—Simple Mail Transfer Protocol
POP3—Post Office Protocol (Version 3)
Telnet—Login (remote terminal)
DNS (Domain Name System)
SNMP—Simple Network Management Protocol
MBS/IP—Multi-purpose Business Security over IP
RIP (Routing Information Protocol)
TCP (Transmission Control Protocol)
UDP (User Datagram Protocol)
IP (Internet Protocol)
ICMP (Internet Control Message Protocol)
OSPF (Open Shortest Path First)
BGP (Border Gateway Protocol)
ARP (Address Resolution Protocol)
RARP (Reverse Address Resolution Protocol)
Net access layer: not included in TCP/IP; e.g. Ethernet IEEE 802.3, TokenBus IEEE 802.4, Token Ring IEEE 802.5, FDDI—Fiber Distributed Data Interface, WLAN IEEE 802.11, PPP—Point-to-Point Protocol IEEE 1394

While there are shown and described presently preferred embodiments of the invention, it is to be distinctly understood that the invention is not limited thereto but may be otherwise variously embodied and practiced within the scope of the following claims.

The invention claimed is:

1. A portable, wearable, implantable, or semi-implantable medical device for use with a web based wireless network, the medical device comprising:
a housing;
a device control unit provided within the housing which controls the medical device;
a wireless web enabler unit provided within the housing; and
a wireless interface control unit provided in the housing and comprising a receiver and a transmitter for receiving and transmitting data wirelessly, wherein: the web enabler unit is coupled to the wireless interface control unit and coupled to the medical device control unit, the wireless interface control unit and the web enabler unit connect the medical device control unit to the web based wireless network, and the web enabler unit is a wireless web server which:

serves at least one configuration web page that allows a browser-equipped client that is connected to the medical device via the web based wireless network to change configuration settings of the medical device control unit in response to a client interaction with the at least one configuration web page, and serves at least one operation mode web page that allows a browser-equipped client that is connected to the medical device via the web based wireless network to change the operation of the medical device control unit in response to a client interaction with the at least one operation web page.

2. A medical device according to claim 1, wherein the medical device is an infusion device for continuously providing medication to a patient carrying the device.

3. A medical device according to claim 2, wherein the infusion device is an insulin pump.

4. A medical device according to claim 1, wherein the medical device is a glucose measurement device of the intermittent stripe measurement type.

5. A medical device according to claim 1, wherein the medical device is a glucose measurement device of the continuous measurement type.

6. A medical device according to claim 1, wherein the medical device is for delivering a liquid in doses.

7. A medical device according to claim 1, wherein the wireless web enabler unit is adapted to work with an application layer control protocol over at least one of TCP, UDP, and TCP and UDP over the internet protocol (IP).

8. A medical device according to claim 1, wherein the wireless web enabler unit is configured to communicate using a network protocol comprising at least one of HTTP, HTTPS, FTP, NTP, SMTP, POP3, Telnet, DNS, SNMP, RIP, IPFIX for applications based on client or server services using at least one of the network protocols.

9. A medical device according to claim 1, wherein the wireless web enabler unit is configured as a web client to use an internet service from a server via the wireless network.

10. A medical device according to claim 1, wherein the wireless web enabler unit is configured as an email service device to allow the medical device to communicate using an email message.

11. A medical device according to claim 1, wherein the wireless web enabler unit is configured as one of a NTP, SNTP, and DTP client to query a time server.

12. A medical device according to claim 1, wherein the wireless interface control unit is configured to communicate using RF technology.

13. A medical device according to claim 12, wherein the wireless interface control unit is configured to communicate using Bluetooth® technology.

14. A medical device according to claim 13, wherein the wireless interface control unit is configured to communicate using a "Bluetooth PAN" profile (TCP/IP over Bluetooth with BNEP).

15. A medical device according to claim 12, wherein the wireless interface control unit is configured to communicate using one of ZigBee, RFID, HomeRF, WLAN, UWB, and NFC.

16. A medical device according to claim 1, wherein the wireless interface control unit is configured to communicate using infrared beams.

17. A medical device according to claim 1, wherein the wireless web enabler unit is based on a single processor.

18. A medical device according to claim 1, wherein the wireless interface control unit is setup on two or more different processors.

19. A medical device according to claim 1, wherein the wireless web enabler unit further comprises an interface between the web enabler unit and the medical device control unit.

20. A medical device according to claim 19, wherein the interface generates commands for the medical device control unit according to data received from the web enabler unit.

21. A medical device according to claim 19, wherein the interface generates data for the web enabler unit according to commands received from the medical device control unit.

22. A medical device according to claim 1, wherein the wireless web enabler unit is configured to prevent data interchange with an unauthorized device using the wireless network.

23. A medical device according to claim 1, wherein the wireless web enabler unit is configured to use secure communication using at least one of VPN, IPsec, SSH (Secure Shell), and SSL (Secure Sockets Layer) protocols.

24. A method for controlling over a web based wireless network a portable, wearable, implantable, or semi-implantable medical device comprising a housing, a device control unit within the housing adapted to control the medical device, a wireless web enabler unit provided within the housing, a wireless interface control unit provided with the housing and comprising a receiver and a transmitter for receiving and transmitting data wirelessly, wherein the web enabler unit is coupled to the wireless interface control unit and coupled to the medical device control unit, wherein the wireless interface control unit and web enabler unit are configured to connect the medical device control unit to the web based wireless network so that the medical device is wirelessly web enabled, wherein the wireless web enabler unit is configured as a web server, the method comprising:

serving at least one configuration web page using the wireless web enabler unit that allows a browser-equipped client that is connected to the medical device via the web based wireless network to change configuration settings of the medical device control unit in response to a client interaction with the at least one configuration web page, and serving at least one operation mode web page using the wireless web enabler unit that allows a browser-equipped client that is connected to the medical device via the web based wireless network to change the operation of the medical device control unit in response to a client interaction with the at least one operation mode web page.

25. A method according to claim 24 wherein the medical device is an insulin pump and the enabled configuration change via the network comprises at least one of insulin pump parameter settings change, insulin pump basal rate change, and insulin pump time and date settings change.

26. A method according to claim 24, further comprising transferring data stored in the medical device control unit to the browser-equipped client in response to a client interaction with the at least one web page.

27. A method according to claim 26 wherein the medical device is at least one of an insulin pump or a blood glucose measurement device and the data comprises at least one of history read-out, firmware version, and status information.

28. A method according to claim 24, further comprising preventing data interchange with an unauthorized client.

29. A method according to claim 24, wherein the browser-equipped client is one of a cell phone, a smart phone, a personal digital assistant (PDA), a laptop computer, a tablet computer (tablet PC), and a desktop computer.

30. A method according to claim 24, wherein the medical device is one of an insulin pump or a blood glucose measurement device, and the network is at least one of a wireless personal, wireless local, and wireless wide area network.

31. A method according to claim 24, wherein the network is a Bluetooth® personal area network (PAN), and the medical device comprises at least one of a group network (GN) and a personal area network user (PANU), and the browser-equipped client comprises at least one of a personal area network user (PANU), a group network (GN) and a network access point (NAP).

32. A method for controlling a portable, wearable, implantable, or semiimplantable medical device, comprising:
 a housing, a device control unit within the housing adapted to control the medical device, and a wireless web enabler unit within the housing comprising:
  i. a wireless interface control unit comprising a receiver and a transmitter for receiving and transmitting data wirelessly; and
  ii. a web enabler unit coupled to the wireless interface control unit and coupled to the medical device control unit,
 wherein the wireless interface control unit and web enabler unit are configured to connect the medical device control unit to a web based wireless network so that the medical device is wirelessly web enabled, wherein the web enabler unit is configured as a web server to serve at least one web page to a browser-equipped client via the wireless network;
 the method comprising:
  connecting to the medical device via the wireless network using the browser-equipped client;
  serving at least one configuration web page from the medical device to the browser-equipped client;
  changing configuration settings of the medical device control unit via the web based wireless network in response to a client interaction of the browser-equipped client with the at least one configuration web page;
  serving at least one operation mode web page from the medical device to the browser-equipped client; and
  changing the operation of the medical device control unit via the web based wireless network in response to a client interaction of the browser-equipped client with the at least one operation mode web page.

33. A method according to claim 32 wherein the medical device is at least one of an insulin pump or a blood glucose measurement device and the controllable functions comprise at least one of bolus delivery, bolus read-out, basal profile change, basal read-out, pump mode change, pump mode read-out, status output, blood glucose measurement value output, and blood glucose measurement value readout.

34. A method according to claim 32, further comprising sending operation information from the medical device control unit to the browser-equipped client without a client interaction with the at least one web page.

35. A method according to claim 34 wherein the medical device is an insulin pump and the operation information includes at least one of alarm output and basal-rate-change output.

36. A method according to claim 32, further comprising preventing data interchange with an unauthorized client.

37. A method according to claim 32 wherein the browser-equipped client is one of a cell phone, a smart phone, a personal digital assistant (PDA), a laptop computer, a tablet computer (tablet PC), and a desktop computer.

38. A method according to claim 32 wherein the network is at least one of a wide area network and wireless wide area network (WAN/WWAN).

39. A method according to claim 32 wherein the network is a Bluetooth® personal area network (PAN), and the medical device comprises at least one of a group network (GN) and a personal area network user (PANU), and the browser-equipped client comprises at least one of a personal area network user (PANU), a group network (GN) and a network access point (NAP).

40. A method according to claim 32 wherein a blood glucose value is uploaded web-based from a blood glucose measurement device to an insulin pump.

41. A method according to claim 32 wherein data of at least one of a blood glucose meter and an insulin pump is web-based stored and retrieved centrally in a central storage media.

42. A method according to claim 32, wherein the medical device provides itself with at least one of time and date by interrogating a time server.

43. A medical device according to claim 32, wherein the medical device represents a group network and the browser-equipped client represents a personal area network user or the medical device represents a personal area network user and the browser-equipped client represents a group network or a network access point.

44. An insulin pump providing different levels of configuration access for a medical personnel access group and a patient access group to the insulin pump over a web based wireless network, the insulin pump comprising:
 a housing;
 a web enabler unit provided within the housing;
 a device control unit provided within the housing which controls the insulin pump; and
 a wireless interface control unit which comprises a receiver and a transmitter that receives and transmits data wirelessly, wherein:
  the web enabler unit is coupled to the wireless interface control unit and coupled to the device control unit,
  the web enabler unit provides a web server, and
  the wireless interface control unit and web enabler unit connect the device control unit to the web based wireless network so that the web server of the web enabler unit:
   serves at least one operation mode web page to a browser-equipped client that is connected to the insulin pump over the wireless network that allows operation of the insulin pump control unit to be changed in response to a client interaction of the browser-equipped client with the at least one operation web page, and
   serves at least one configuration web page to a browser-equipped client that is connected to the insulin pump over the wireless network, wherein if the browser-equipped client is an authorized user of the medical access group, then the authorized user may change configuration settings of the insulin pump control unit in response to a client interaction of the browser-equipped client with the at least one configuration web page.

45. An insulin pump according to claim 44, wherein if the browser-equipped client is an authorized user of the patient access group, then the authorized user may change a limited number of the configuration settings of the insulin pump control unit in response to a client interaction of the browser-equipped client with the at least one configuration web page.

* * * * *

UNITED STATES PATENT AND TRADEMARK OFFICE
CERTIFICATE OF CORRECTION

| | | |
|---|---|---|
| PATENT NO. | : 8,971,958 B2 | Page 1 of 1 |
| APPLICATION NO. | : 11/870216 | |
| DATED | : March 3, 2015 | |
| INVENTOR(S) | : Marcel Frikart et al. | |

It is certified that error appears in the above-identified patent and that said Letters Patent is hereby corrected as shown below:

IN THE SPECIFICATION

Col. 4, Line 15,
"In some preferred embodiment, the method comprises" should read
--In some preferred embodiments, the method comprises--;

Col. 5, Line 40,
"devices as well. A preferred a pocket size or less than pocket" should read
--devices as well. A preferred pocket size or less than pocket--;

Col. 5, Line 66,
"example, to click on setting suggested by the web-page or to" should read
--example, to click on settings suggested by the web-page or to--;

Col. 6, Line 3,
"may be accessible only to medical personal or may be acces-" should read
--may be accessible only to medical personnel or may be acces- --;

Col. 6, Line 5,
"personal. Entering the configuration settings on the web-page" should read
--personnel. Entering the configuration settings on the web-page--;

Col. 6, Line 13,
"FIG. 9 shows an example of an configuration page pro-" should read
--FIG. 9 shows an example of a configuration page pro- --; and Col. 7, Line 12,
"or motors that provide the actual pumping of the content of a" should read
--or motors that provide the actual pumping of the content of an--.

Signed and Sealed this
Sixteenth Day of February, 2016

Michelle K. Lee
*Director of the United States Patent and Trademark Office*